United States Patent [19]

Sakurada et al.

[11] Patent Number: 4,513,166
[45] Date of Patent: Apr. 23, 1985

[54] PROCESS FOR THE LOW POLYMERIZATION OF ISOBUTENE

[75] Inventors: Satoshi Sakurada, Omiya; Takao Hashimoto, Saitama; Nobuaki Tagaya, Kawagoe; Tsugio Maeshima, Saitama; Kayako Ueda, Tokyo; Masahiro Kokubo, Saitama, all of Japan

[73] Assignee: Toa Nenryo Kogyo Kabushiki Kaisha, Tokyo, Japan

[21] Appl. No.: 597,821

[22] Filed: Apr. 6, 1984

Related U.S. Application Data

[62] Division of Ser. No. 476,015, Mar. 15, 1983, Pat. No. 4,454,367.

[30] Foreign Application Priority Data

Mar. 23, 1982 [JP] Japan .................................. 57-44684
Mar. 26, 1982 [JP] Japan .................................. 57-47316

[51] Int. Cl.$^3$ ................................................ C07C 7/01
[52] U.S. Cl. .................................... 585/832; 585/533; 502/78
[58] Field of Search ............... 585/510, 533, 809, 832; 502/78

[56] References Cited

U.S. PATENT DOCUMENTS

| | | | |
|---|---|---|---|
| 2,552,692 | 5/1951 | Schulze et al. | 585/832 |
| 3,452,113 | 6/1969 | Godin | 585/533 |
| 3,960,978 | 6/1976 | Givens et al. | 585/533 |
| 4,182,692 | 1/1980 | Kiovsky et al. | 502/78 |
| 4,313,016 | 1/1982 | Manning | 585/832 |
| 4,454,367 | 6/1984 | Sakurada et al. | 585/832 |

FOREIGN PATENT DOCUMENTS

| | | | |
|---|---|---|---|
| 503951 | 6/1954 | Canada | 585/832 |
| 451681 | 12/1972 | U.S.S.R. | 585/832 |
| 798083 | 9/1978 | U.S.S.R. | 585/832 |

Primary Examiner—Delbert E. Gantz
Assistant Examiner—A. Pal
Attorney, Agent, or Firm—Wenderoth, Lind & Ponack

[57] ABSTRACT

1-Butene and isobutene are effectively separated without isomerization of 1-butene by contacting an isobutene-containing hydrocarbon mixture with a solid acid catalyst having a solid acid quantity of 0.05 to 0.25 mmol/g of solid acid catalyst, represented by the adsorption quantity of pyridine, thus low-polymerizing selectively isobutene and then separating the low polymers of isobutene from 1-butene.

1 Claim, 3 Drawing Figures

PROCESS FOR THE LOW POLYMERIZATION OF ISOBUTENE

This is a divisional application of Ser. No. 476,015, filed Mar. 15, 1983, now U.S. Pat. No. 4,454,367.

BACKGROUND OF THE INVENTION

1. Field of the Invention

This invention relates to a process for the low polymerization of isobutene using a solid acid catalyst, in particular, high silica mordenite catalyst with a specified solid acid quantity, and more particularly, it is concerned with a process for the selective low polymerization of only isobutene in an isobutene-containing hydrocarbon mixture.

2. Description of the Prior Art

In the low polymerization of isobutene in a hydrocarbon mixture containing isobutene, it is well known to contact the hydrocarbon mixture with a solid acid catalyst such as silica.alumina, zeolite or cation exchange resin. This method is used for the removal of isobutene in $C_4$ hydrocarbon mixtures.

For example, there have hitherto been proposed (1) a method comprising contacting a $C_4$ hydrocarbon mixture with an isomerization catalyst such as palladium, platinum or nickel to isomerize 1-butene in 2-butene, further contacting with a solid acid catalyst such as activated clay or silica.alumina to low-polymerize isobutene and separating the resulting low polymers (Japanese Patent Application OPI (Kokai) No. 8201/1976), (2) a method comprising contacting a $C_4$ hydrocarbon mixture with a crystalline molecular sieve (10X Molecular Sieve) having effective pores of about 8 to 8.2 Å to remove isobutene (Japanese Patent Publication No. 42803/1972), (3) a method comprising contacting a $C_4$ hydrocarbon mixture with a synthetic zeolite (ZSM-4) to low-polymerize selectively isobutene (Japanese Patent Publication No. 29121/1976) and (4) a method comprising feeding a $C_4$ hydrocarbon mixture to a distilling column packed with a cation exchange resin, low-polymerizing isobutene and separating and removing the low polymers from the bottom thereof (U.S. Pat. No. 4,215,011).

However, any of these methods is not suitable as a method of producing 1-butene free from isobutene since 1-butene contained in the $C_4$ hydrocarbon mixture tends to be isomerized in 2-butene.

SUMMARY OF THE INVENTION

It is an object of the present invention to provide an improved process for the low polymerization of isobutene using a solid acid catalyst.

It is another object of the present invention to provide a process for selectively polymerizing isobutene contained in 1-butene as an impurity.

It is a further object of the present invention to provide a method of purifying 1-butene containing isobutene.

It is a still further object of the present invention to provide a process for the production of high silica mordenites suitable for use as a solid acid catalyst in the low polymerization of isobutene.

These objects can be attained by a process for the low polymerization of isobutene, which comprises contacting an isobutene-containing hydrocarbon mixture with a solid acid catalyst having a solid acid quantity of 0.05 to 0.25 mmol/g.solid acid catalyst, represented by the adsorption of pyridine, the solid acid catalyst being for example prepared by converting mordenite into hydrogen-exchanged type or its precursor, heat-treating at 600° C. or higher in the presence of steam and then contacting with an acid.

BRIEF DESCRIPTION OF THE DRAWINGS

The accompanying drawings are to illustrate the merits and principle of the present invention.

DETAILED DESCRIPTION OF THE INVENTION

Figure 1:
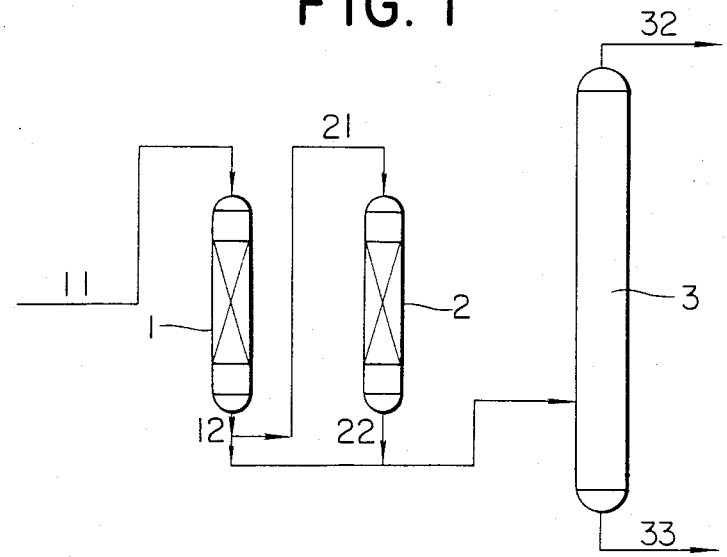
FIG. 1 is a flow diagram to illustrate a process for the low polymerization of isobutene using a specified solid acid catalyst according to the present invention.

The inventors have made various efforts to develop a catalyst capable of polymerizing selectively only isobutene without exhibiting activity in the isomerization of 1-butene in 2-butene, and consequently, have reached the present invention. We have also succeeded in removing effectively isobutene in 1-butene without loss of the 1-butene by polymerizing selectively isobutene contained as an impurity in 1-butene using the catalyst of the present invention, and separating and removing isobutene as low polymers.

That is, the present invention provides a process for the low polymerization of isobutene, which comprises contacting an isobutene-containing hydrocarbon mixture with a solid acid catalyst having a solid acid quantity of 0.05 to 0.25 millimol per 1 g of solid acid catalyst, represented by the adsorption quantity of pyridine.

As the solid acid catalyst of the present invention, there can be used any solid acid catalyst whose solid acid quantity can be determined by the pyridine adsorption method. Above all, a the solid catalyst having a pyridine adsorption quantity of 0.05 to 0.25 mmol per 1 g of a solid acid catalyst is capable of activating selectively only tertiary carbon atoms in the case of activating the carbon of a relatively lower olefin to give carbonium ions.

In the solid acid catalyst whose solid acid quantity is controlled, in particular, a high silica content mordenite catalyst with an $SiO_2$ to $Al_2O_3$ mole ratio of 50 to 200 is preferable as a catalyst capable of polymerizing selectively only isobutene and having no activity in the isomerization of 1-butene to 2-butene.

The high silica mordenite catalyst whose solid acid quantity is controlled and which can be used in the present invention is generally obtained by converting natural or synthetic mordenite having the following unit cell:

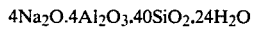

$4Na_2O.4Al_2O_3.40SiO_2.24H_2O$ into a hydrogen exchanged type or its precursor, subjecting it to a hydrothermal treatment at a high temperature in the presence of steam and then to extraction of aluminum with a strong acid.

In general, in order to apply such mordenite effectively as a catalyst for conversion of hydrocarbons, it is required to give a property as a solid acid and to raise the reactivity thereof by a cation exchange treatment wherein the most part of cations contained therein is ion-exchanged with catalytically active metallic ions or hydrogen ions.

Conversion of mordenite into a hydrogen type mordenite by the cation exchange operation can also be accomplished in conventional manner by ammonium ion exchange with ammonium chloride or by treating with a relatively weak acid, since the mordenite itself has a relatively high silica to alumina ratio from the first. Furthermore, it is well known that in the case of treating with a relatively strong acid, not only a cation exchange reaction but also removal of aluminum in the crystal lattice take place to increase further the silica to alumina ratio in the mordenite and the thus treated mordenite, when used as a catalyst, has a high reactivity in hydrocarbon conversion reactions such as hydrocracking, thermal cracking, isomerization, disproportionation and the like.

When mordenite is treated to increase the silica/alumina ratio by the prior art method, however, the solid acid quantity is too large or too small and control of the solid acid quantity is impossible.

The inventors have made studies on a method of controlling the solid acid quantity of a crystalline alumino-silicate and consequently, have found a method of preparing a high silica mordenite having a silica/alumina ratio of 50 to 200 and a specified solid acid quantity or solid acid strength distribution whereby selective conversion of hydrocarbons is made possible, which comprises subjecting mordenite to a heat treatment in the presence of steam and then contacting the treated mordenite with a strong acid.

That is to say, the present invention is characterized by the use of a high silica mordenite with a specified solid acid quantity, which is obtained by converting mordenite into a hydrogen exchanged type or its precursor, subjecting to a treatment at a temperature of at least 600° C. in the presence of steam and then contacting with an acid.

The raw material mordenite used herein can be any of natural and synthetic mordenites. The mordenite is converted into a hydrogen ion type or hydrogen ion type precursor prior to hydrothermal treatment, but the raw material mordenite can be combined with any metal ions, i.e. alkali metal ions or alkaline earth metal ions. The hydrogen exchanged type or hydrogen exchanged type precursor can be prepared by subjecting the above described raw material mordenite to an exchange method using an aqueous acid solution or ammonium salt solution. For example, hydrochloric acid, sulfuric acid, nitric acid and the like is used as the acid. The acid concentration is preferably at least 0.5 normality. The hydrogen ion exchange reaction is preferably carried out at room temperature to 100° C. and heating is preferably employed to accelerate the conversion reaction.

The hydrothermal reaction is effected by a heat treatment in the presence of steam, during which the partial pressure of steam and the treatment temperature are so chosen as to control the silica/alumina ratio to 50 to 200 as well as the solid acid quantity.

For the purpose of adjusting the pyridine adsorption quantity to 0.05 to 0.25 mmol per 1 g of high silica mordenite, it is desirable to effect the hydrothermal treatment under a steam partial pressure of 1 to 50%, preferably 5 to 40% at a temperature of 600° to 1000° C., preferably 650° to 750° C. At a temperature of lower than this range, the solid acid quantity cannot be controlled. In the absence of steam, only a mordenite with a larger solid acid quantity can be obtained and if the steam partial pressure exceeds this range, other reactions than the aluminum removing reaction tend to occur often whereby to decrease markedly the solid acid quantity.

The hydrothermal treatment is generally carried out in 1 to 10 hours, preferably 2 to 5 hours with satisfactory results. Following the hydrothermal treatment, an acid-extraction treatment is carried out so as to remove $AlOH^{2+}$ dislocated from the mordenite skeleton structure by the hydrothermal treatment and being present in so-called nests or aluminum atoms positioned in a relatively weak skeleton structure. Examples of the acid used in the acid-extraction treatment are inorganic acids such as hydrochloric acid, nitric acid, sulfuric acid and phosphoric acid, and organic acids such as acetic acid, chloroacetic acid, trichloroacetic acid, citric acid, tartaric acid and oxalic acid. Of these acids, mineral acids such as hydrochloric acid, sulfuric acid and nitric acid are preferable. When using these acids in the extraction treatment, an acid concentration of at least 4N, preferably at least 6N is preferable. The acid-extraction treatment is preferably carried out at a temperature ranging from room temperature to 100° C.

The thus acid-extraction mordenite is preferably subjected to a calcining treatment under more moderate conditions than in the hydrothermal treatment, i.e. at 400° to 700° C., preferably 500° to 650° C. to stabilize the unstable crystal state.

The thus obtained high silica mordenite with a pyridine adsorption quantity of 0.05 to 0.25 mmol per 1 g of mordenite and a silica/alumina ratio of 50 to 200 can be used as the reaction catalyst of the present invention as it is or after forming.

The solid acid quantity or solid acid strength of the high silica content mordenite obtained in this way is determined by the adsorption-desorption method. That is to say, a basic material is caused to adsorb on solid acid sites, followed by raising the temperature, and the desorbed basic material is determined, which corresponds to the adsorption quantity. The adsorption quantity of the basic material is directly related with the solid acid quantity and the temperature at which the basic material is desorbed is directly related with the solid acid strength. Thus, a relative solid acid quantity and solid acid strength distribution can be given.

Examples of the basic material used in the adsorption-disorption method are ammonia, pyridine and n-butylamine. Above all, pyridine is preferable, because the desorbed quantity can readily be determined by the hydrogen ion detecting method and pyridine is caused to adsorb on solid acid sites, i.e. Brønsted Acid sites as pyridinium ion and to adsorb on Lewis Acid sites as coordinate bond pyridine to determine the acid quantity relatively correctly.

According to the process of the present invention, there is obtained a high silica mordenite with a pyridine adsorption quantity of 0.05 to 0.25 mmol per 1 g of mordenite.

When the steam partial pressure is increased and the treatment temperature is raised in the hydrothermal treatment, the solid acid quantity is decreased, while when the steam partial pressure is decreased and the treatment temperature is lowered, the solid acid quantity is increased.

The solid acid catalyst, in particular, high silica mordenite used as a catalyst in the process of the present invention has the feature that deterioration of the catalytic performance scarcely takes place even when used for a long time, but its catalytic activity can be held for a further long time by contacting previously with hydrocarbons at a temperature of higher than the reaction temperature before it is used as a catalyst.

Any hydrocarbon can be used for the pretreatment, but unsaturated hydrocarbons such as olefins, diolefins and aromatic hydrocarbons, in particular, hydrocarbon mixtures as a raw material are preferable from the standpoint of operation.

The pretreatment is preferably carried out in liquid phase or gaseous phase at a temperature of higher than the reaction temperature of the main reaction (catalytic reaction of raw material hydrocarbons) and lower than 300° C. for 10 minutes to 5 hours. More preferably, the pretreatment is carried out under conditions of: liquid phase, reaction temperature 140°-200° C., reaction time 0.5-2 hrs, and liquid hourly space velocity (LHSV) 1–20 hr$^{-1}$.

As the hydrocarbon mixture used in the present invention, there can be used any hydrocarbon mixture containing isobutene and n-butene, but on a commercial scale, it is preferable to use, for example, $C_4$ hydrocarbon mixtures obtained in refining, cracking and reforming of oils, butanebutene fractions obtained by removing butadiene from $C_4$ fraction byproduced in the production of ethylene by thermal cracking of oils or $C_4$ hydrocarbon mixtures obtained by dehydrogenation of hydrocarbon mixtures containing n-butane and isobutane. The $C_4$ hydrocarbon mixtures can be used as it is.

These hydrocarbons include generally, in addition to n-butenes (1-butene, trans-2-butene, cis-2-butene) and isobutene, n-butane, isobutane, butadiene and trace amounts of $C_3$ hydrocarbons and $C_5$ hydrocarbons. The contents of these components are not particularly limited, but in the case of aiming at producing high purity 1-butene, it is desirable to use hydrocarbon mixtures containing at least 20 mole % of n-butenes and 0.1 to 50 mole % of isobutene.

Low polymers of isobutene are obtained by contacting isobutene with a catalyst consisting of the hydrogen type crystalline aluminosilicate according to the present invention, during which the polymerization conditions are a gaseous phase or a liquid phase reaction, a reaction temperature of 20°-180° C. and a reaction pressure atmospheric pressure of 100 Kg/cm² and the preferable polymerization conditions are a liquid phase reaction, a reaction temperature of 60°-140° C. and a pressure capable of holding a liquid phase at 10–50 Kg/cm². In the case of the liquid phase reaction, LHSV is 0.01 to 50 hr$^{-1}$, preferably 0.1 to 10 hr$^{-1}$ as to the raw material.

According to the present invention, isobutene contained in a raw material is substantially converted into low polymers of dimer, trimer or more and 1-butene is scarcely isomerized. The low polymers of isobutene are further separated and removed by any of known methods. Thus, a substantially isobutene-free fraction can be obtained, from which 1-butene and/or 2-butene can further be recovered in conventional manner without use of any specified method.

In the process of the present invention, isobutene contained in a raw material hydrocarbon mixture can substantially be converted into low polymers of dimer, trimer and more, which can readily be separated from $C_4$ hydrocarbons, which substantially prevents isomerization of 1-butene in 2-butene and the loss of n-butenes, and accordingly, the isobutene can completely be removed through combination of a step of removing the low polymers. Thus, a high purity 1-butene and/or 2-butene which is substantially free from isobutene can be recovered from the fraction from which the polymers have been removed.

As apparent from the foregoing illustration, the process of the present invention is available for purification of 1-butene, since isobutene can selectively be low-polymerized without isomerization of 1-butene and the low polymers of isobutene can readily be separated from the isobutene. One embodiment of this process is shown in the accompanying drawings.

Referring to FIG. 1, a 1-butene fraction containing isobutene as an impurity is fed from pipe 11 to isobutene polymerization column 1 packed with a catalyst whose solid acid quantity is controlled, where the isobutene contained in the 1-butene fraction is selectively low-polymerized, and then withdrawn via pipe 12. This fraction is further fed from pipe 21 to second isobutene polymerization column 2 packed similarly with a catalyst whose solid acid quantity is controlled, where the residual isobutene is low-polymerized. The 1-butene fraction containing low polymers of isobutene is then fed through pipe 31 to distilling column 3, from which the low polymers of isobutene are withdrawn via pipe 33 and high purity 1-butene substantially free from isobutene is separated and recovered by distillation.

In FIG. 1, the embodiment of using two isobutene polymerization columns has been illustrated, but in a case where isobutene is contained in a trace amount, one isobutene polymerization column is sufficient for achieving the object and if necessary, three or more columns can be used.

Figure 2:
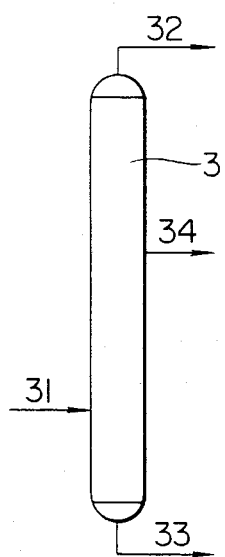
FIG. 2 and FIG. 3 are flow diagrams to illustrate processes for separating components processed by the present invention.
Figure 3:
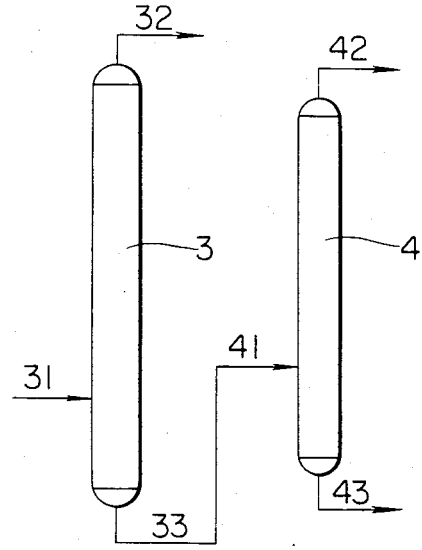

When 2-butene is contained in a 1-butene fraction, separation of 1-butene and 2-butene is carried out by adjusting the operation condition of distilling column 3 so that 2-butene is withdrawn from pipe 33 together with the low polymers of isobutene in FIG. 1. Moreover, as shown in FIG. 2, distilling column 3 can be used which is so designed that 2-butene be withdrawn from pipe 34. In FIG. 1, a mixture of low polymers of isobutene and 2-butene is withdrawn through pipe 33 and then fed via pipe 41 to distilling column 4 as shown in FIG. 3, where 2-butene and the low polymers of isobutene are readily separated by distillation and respectively withdrawn from pipe 42 and pipe 43.

The following examples are given in order to illustrate the present invention in greater detail without limiting the same.

EXAMPLE 1

Preparation of high silica mordenite catalyst 100 g of 1/16 inch pellets of a commercially sold highly crystalline sodium type mordenite (commercial name: Zeolon 900 Na manufactured by Norton Co.) was immersed in 500 ml of 1N HCl and stirred at 80° C. for 1 hour. Then, the acid solution was removed by decantation and 500 ml of new 1N HCl was added, followed by stirring at 80° C. for 1 hour. After removing the hydrochloric acid solution, the reaction product was washed with warm water until no chloride ion was found and dried by hot air at 110° C. to obtain a hydrogen ion exchanged type precursor of mordenite. The resulting hydrogen ion exchanged type precursor was subjected to a hydrothermal treatment under a steam partial pressure of 30% of for 4 hours at 650° C., the temperature being gradually raised. After cooling, the precursor was subjected to a refluxing treatment at 90° C. for 6 hours using 500 ml of 12N HCl to extract aluminum. After removing the hydrochloric acid solution, the product was washed with warm water until no chloride ion was found and then dried by hot air at 110° C. After air drying, the product was calcined at 650° C. for 3 hours in a muffle furnace to thus obtain a high silica content mordenite with a composition and silica/alumina ratio as shown in Table 1.

The thus obtained high silica mordenite was ground in a size of 30 to 100 mesh and calcined at 500° C. for 1 hour to remove adsorbed components. 0.075 g of the mordenite was taken by precisely weighing and charged in a reactor. On the other hand, a pyridine-charged bubbler was immersed in a water bath held at a constant temperature, i.e. 15.5° C. Nitrogen gas was bubbled in the pyridine and fed to the mordenite catalyst charged in the reactor, where pyridine was caused to absorb on the catalyst at room temperature.

With flowing nitrogen gas, the reactor was heated gradually to 300° C. and held at 300° C. until the pyridine adsorbed physically was desorbed. When the desorption of the pyridine was not found by gas chromatography, the temperature of the reactor was raised at a rate of 10° C./min from 300° C. to 950° C. and during the same time, the desorbed pyridine was determined by gas chromatography. The quantity of the desorbed pyridine is in proportion to the solid acid quantity of the mordenite, as shown in Table 1.

Catalytic reaction

A $C_4$ hydrocarbon mixture consisting of 26.2 mole % of butane, 1.3 mole % of isobutene, 7.5 mole % of 1-butene and 65 mole % of 2-butene was fed to a cylindrical reactor packed with the above described catalyst and subjected to a catalytic reaction in liquid phase at a reaction temperature of 80° C., a reaction pressure of 35 Kg/cm$^2$ (compressed by nitrogen gas) and LHSV of 3.0 hr$^{-1}$.

After 16 hours from the start of reaction, the hydrocarbon mixture taken at the outlet of the reactor was analyzed thus obtaining the results shown in Table 1. With the passage of the reaction time, conversion of the isobutene was traced to seek the degradation coefficient $\alpha$ from $k = k_0 e^{\alpha t}$ where k is an isobutene dimerization rate constant at time t, $k_0$ is an initial rate constant obtained by extrapolation and $\alpha$ is a degradation coefficient. The results are shown in Table 1.

COMPARATIVE EXAMPLE 1

The hydrogen ion exchanged type precursor obtained in Example 1 was calcined at 650° C. for 4 hours using a muffle furnace, and then subjected to extraction with hydrochloric acid and calcination in an analogous manner to Example 1 to obtain a mordenite catalyst with a pyridine adsorption quantity, composition and silica/alumina ratio as shown in Table 1. Using this catalyst, a catalytic reaction was carried out in an analogous manner to Example 1, thus obtaining the results shown in Table 1.

COMPARATIVE EXAMPLE 2

A mordenite catalyst was prepared in an analogous manner to Example 1 except using a steam partial pressure of 100%, treatment temperature of 700° C. and treatment time of 3 hours in the hydrothermal treatment of Example 1, and then subjected to a catalytic reaction, thus obtaining the results shown in Table 1.

COMPARATIVE EXAMPLE 3

A mordenite catalyst was prepared in an analogous manner to Example 1 except using a steam partial pressure of 65%, treatment temperature of 650° C. and treatment time of 3 hours in the hydrothermal treatment of Example 1 and then subjected to a catalytic reaction to thus obtain a results as shown in Table 1.

EXAMPLE 2

Example 1 was repeated except using nitric acid instead of the hydrochloric acid in the acid treatment of Example 1 to obtain results shown in Table 1.

EXAMPLE 3

Example 1 was repeated except using sulfuric acid instead of the hydrochloric acid in the acid treatment of Example 1 to thus obtain results shown in Table 1.

EXAMPLE 4

Preparation of catalyst 67 g of aluminum sulfate, 19.7 g of conc. $H_2SO_4$ and 140 g of sodium chloride were dissolved in 1500 g of pure water, to which 490 g of water glass (JIS No. 3) was then added to form an aqueous reaction mixture with a composition of $2.5Na_2O.Al_2O_3.23SiO_2.99H_2O$. This reaction mixture was aged at room temperature for about 1 hour, charged in an autoclave, rapidly heated and held at 180° C. for 20 hours. The thus resulting solid product was cooled to room temperature, filtered, washed adequately with water and dried at 110° C. A part of the product was calcined at 700° C. in the air and then subjected to adsorption of water at room temperature and to chemical analysis. The resulting synthetic mordenite had the following composition:

| | |
|---|---|
| Ignition Loss at 800° C. | 10.0% by weight |
| $SiO_2$ | 79.1% by weight |
| $Al_2O_3$ | 5.96% by weight |
| $Na_2O$ | 3.51% by weight |
| $SiO_2/Al_2O_3$ (mole ratio) | 22.6 |

In addition, it was found from the spacing in X-ray powder diffraction analysis that the product had the crystalline structure of mordenite.

100 g of the resulting synthetic mordenite was processed in the same manner as in Example 1 to thus obtain a high silica mordenite with a composition and pyridine adsorption quantity as shown in the following:

| Composition | |
|---|---|
| Ignition Loss at 800° C. | 3.2% by weight |
| $SiO_2$ | 95.1% by weight |
| $Al_2O_3$ | 1.22% by weight |
| $Na_2O$ | 0.11% by weight |
| $SiO_2/Al_2O_3$ (mole ratio) | 133 |

Catalytic Reaction

Using this catalyst, a catalytic reaction was carried out in an analogous manner to Example 1, thus obtaining the results shown in Table 1.

EXAMPLE 5

Example 1 was repeated except using a steam partial pressure of 5%, a treatment of 700° C. and a treatment time of 3 hours in the hydrothermal treatment of Example 1 to obtain the results shown in Table 1.

EXAMPLE 6

Example 1 was repeated except using a steam partial pressure of 20%, a treatment temperature of 700° C. and a treatment time of 3 hours in the hydrothermal treatment of Example 1 to thus obtain the results shown in Table 1.

COMPARATIVE EXAMPLE 4

The hydrogen ion exchanged type precursor obtained in Example 1 was calcined at 600° C. for 3 hours in a muffle furnace to obtain a hydrogen ion exchanged type mordenite. Using this catalyst, a catalytic reaction was carried out in an analogous manner to Example 1, thus obtaining the results shown in Table 1.

EXAMPLE 7

A part of the catalyst of Example 5 was retreated using the same hydrothermal conditions as those of Example 5. The results were shown in Table 1.

EXAMPLE 8

Example 1 was repeated except using a steam partial pressure of 45%, a treatment temperature of 660° C. and a treatment time of 4 hours in the hydrothermal treatment of Example 1 to obtain the results shown in Table 1

EXAMPLE 9

Example 1 was repeated except using a steam partial pressure of 20%, a treatment temperature of 630° C. and a treatment time of 3 hours in the hydrothermal treatment of Example 1 to obtain the results shown in Table 1.

EXAMPLE 10

Example 4 was repeated except using a steam partial pressure of 45%, a treatment temperature of 660° C. and a treatment time of 4 hours in the hydrothermal treatment of Example 4 to obtain the results shown in Table 1.

TABLE 1

| | Mordenite Catalyst | | | | | | | | | |
|---|---|---|---|---|---|---|---|---|---|---|
| | Pyridine Adsorption Quantity (mmol/g. mordenite) | Composition | | | | | Isobutene Conversion (mole %) | n-Butene Loss (mole %) | $k_o$ | $\alpha$ (1/hr) |
| | | Ignition Loss at 800° C. (wt %) | $SiO_2$ (wt %) | $Al_2O_3$ (wt %) | $Na_2O$ (wt %) | $SiO_2/Al_2O_3$ (wt %) | | | | |
| Example No. | | | | | | | | | | |
| 1 | 0.113 | 5.3 | 92.7 | 1.75 | 0.17 | 90 | 89.3 | 3.2 | 9.8 | 0.0032 |
| 2 | 0.112 | 4.4 | 93.8 | 1.50 | 0.15 | 106 | 91.0 | 4.3 | 11.5 | 0.0019 |
| 3 | 0.118 | 4.5 | 93.1 | 1.79 | 0.12 | 96 | 86.7 | 2.9 | 8.0 | 0.0041 |
| 4 | 0.108 | 3.2 | 95.1 | 1.22 | 0.11 | 133 | 91.2 | 3.8 | 12.0 | 0.0033 |
| 5 | 0.121 | 5.5 | 92.0 | 1.81 | 0.16 | 86 | 88.1 | 4.2 | 8.8 | 0.0029 |
| 6 | 0.111 | 4.3 | 94.1 | 1.50 | 0.13 | 107 | 92.1 | 5.1 | 13.5 | 0.0041 |
| 7 | 0.119 | 5.0 | 93.6 | 1.33 | 0.07 | 120 | 90.3 | 2.5 | 12.9 | 0.0018 |
| 8 | 0.098 | 2.8 | 96.0 | 1.09 | 0.14 | 152 | 85.3 | 2.9 | 7.6 | 0.0035 |
| 9 | 0.230 | 5.9 | 91.9 | 1.98 | 0.16 | 79 | 93.1 | 5.3 | 14.0 | 0.0053 |
| 10 | 0.095 | 2.9 | 95.9 | 0.92 | 0.14 | 177 | 81.2 | 2.8 | 5.1 | 0.0037 |
| Comparison | | | | | | | | | | |
| 1 | 0.360 | 8.6 | 86.5 | 4.1 | 0.18 | 36 | 48.0 | 12.3 | 1.2 | 0.0052 |
| 2 | 0.041 | 3.5 | 95.2 | 1.20 | 0.11 | 135 | 26.0 | 2.1 | 0.3 | 0.0081 |
| 3 | 0.042 | 3.9 | 94.4 | 1.51 | 0.14 | 106 | 68.0 | 25.6 | 3.5 | 0.0076 |
| 4 | 0.544 | 6.8 | 80.5 | 10.0 | 1.06 | 13.7 | 76.5 | 38.1 | 16.0 | 0.190 |

What is claimed is:

1. A method of purifying 1-butene containing isobutene, which comprises contacting an isobutene-containing hydrocarbon mixture with a solid acid catalyst having a solid acid quantity of 0.05 to 0.25 mmol/g.solid acid catalyst, represented by the adsorption of pyridine, thus selectively low-polymerizing isobutene and then separating the low polymers of isobutene from the 1-butene, said solid acid catalyst being a high silica mordenite having an $SiO_2/Al_2O_3$ mole ratio of 50 to 200.

* * * * *